United States Patent
Dams et al.

(10) Patent No.: US 10,968,156 B2
(45) Date of Patent: Apr. 6, 2021

(54) PROCESS FOR THE MANUFACTURING OF A 3-HALOPROPIONYL HALIDE IN A FLOW REACTOR

(71) Applicant: 3M INNOVATIVE PROPERTIES COMPANY, St. Paul, MN (US)

(72) Inventors: Rudolf J. Dams, Antwerp (BE); Rudy W. Van Campenhout, Hoboken (BE); Matthias Conradi, Hemsloh (DE); Marine Movsisyan, Melle (BE); Christian Stevens, Merelbeke (BE)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 16/766,887

(22) PCT Filed: Dec. 12, 2018

(86) PCT No.: PCT/IB2018/059956
§ 371 (c)(1),
(2) Date: May 26, 2020

(87) PCT Pub. No.: WO2019/123126
PCT Pub. Date: Jun. 27, 2019

(65) Prior Publication Data
US 2020/0361844 A1    Nov. 19, 2020

(30) Foreign Application Priority Data

Dec. 20, 2017  (EP) .................................. 17208982

(51) Int. Cl.
*C07C 45/63*  (2006.01)
(52) U.S. Cl.
CPC .................... *C07C 45/63* (2013.01)
(58) Field of Classification Search
CPC ................................................ C07C 45/63
See application file for complete search history.

(56) References Cited

U.S. PATENT DOCUMENTS

| | | | |
|---|---|---|---|
| 2,013,988 | A | 9/1935 | Meder |
| 4,096,182 | A | 6/1978 | Rupp |
| 2010/0185013 | A1 | 7/2010 | Pinnow |
| 2011/0071307 | A1 | 3/2011 | Ishiyama |
| 2011/0087041 | A1 | 4/2011 | Ishiyama |
| 2017/0120499 | A1 | 5/2017 | Li |

FOREIGN PATENT DOCUMENTS

| | | |
|---|---|---|
| EP | 1600276 | 7/2008 |
| JP | S63-063636 | 3/1988 |
| JP | H11-199540 | 7/1999 |
| JP | 2003-026630 | 1/2003 |
| WO | WO 2005-092842 | 10/2005 |
| WO | WO 2009-005937 | 1/2009 |
| WO | WO 2017-147040 | 8/2017 |
| WO | WO 2019-123125 | 6/2019 |
| WO | WO 2019-123127 | 6/2019 |

OTHER PUBLICATIONS

Chevalier, Micro Reactors for Industrial Multiphase Applications: Test Reactions to Develop Innovative Glass Microstructure Designs, Chimica Oggi Chemistry Today, Mar.-Apr. 2008, vol. 26, No. 2, pp. 38-42.
Cvetovich, Formation of Acrylanilides, Acrylamides, and Amides Directly from Carboxylic Acids Using Thionyl Chloride in Dimethylacetamide in the Absence of Bases Organic Process Research & Development, 2006, vol. 10, No. 5, pp. 944-946.
Imai, "Studies on Alkyl Ketene Dimers. VI," Journal of Japan Oil Chemists' Society, vol. 10, No. 7, Jan. 1, 1961, pp. 435-440. XP055484965.
Krtschil, "Cost Analysis of a Commercial Manufacturing Process of a Fine Chemical Compound Using Micro Process Engineering," CHIMIA International Journal for Chemistry 2006, vol. 60, No. 9, pp. 611-617.
Movsisyan, "Safe, Selective, and High-Yielding Synthesis of Acryloyl Chloride in a Continuous-Flow System," ChemSusChem, 2016, vol. 9, No. 15, pp. 1945-1952.
Movsisyan, "Taming Hazardous Chemistry by Continuous Flow Technology", Chemical Society Reviews, 2016, vol. 45, No. 18, pp. 4892-4928.
Schaber "Economic Analysis of Integrated Continuous and Batch Pharmaceutical Manufacturing: A Case Study," Industrial & Engineering Chemistry Research, 2011, vol. 50, No. 17, pp. 10083-10092.
Stempel, The Preparation of Acrylyl Chloride, Journal of American Chemical Society,1950, vol. 72, p. 2299-2300.
Wiles, "Recent Advances in Micro Reaction Technology," Chemical Communications, 2011, vol. 47, pp. 6512-6535.
Extended EP Search Report for EP Application No. 17208948.4, dated Jun. 28, 2018, 7 pages.
Extended EP Search Report for EP Application No. 17208982.3, dated May 22, 2018, 5 pages.

(Continued)

*Primary Examiner* — Sikarl A Witherspoon
(74) *Attorney, Agent, or Firm* — Carolyn A. Fischer

(57) ABSTRACT

The present disclosure relates to a process for the manufacturing of a 3-5 halopropionylhalide, wherein the process comprises the steps of: a) providing a flow reactor comprising a reaction chamber; b) providing reactants comprising: i. acrylic acid; ii. a reaction co-agent selected from the group consisting of N,N-0 disubstituted amides; and iii. a halogenating agent; and c) incorporating the reactants into the reaction chamber of the flow reactor, thereby forming a reaction product stream comprising a 3-halopropionyl-halide; wherein the molar ratio of acrylic acid to the halogenating agent is 1 to at least 5 0.8; wherein the temperature of the reaction chamber of the flow reactor is greater than 60° C.; and wherein the residence time of the reaction product stream comprising the 3-halopropionylhalide in the reaction chamber of the flow reactor is greater than 10 minutes.

17 Claims, No Drawings

(56) References Cited

OTHER PUBLICATIONS

Extended EP Search Report for EP Application No. 17208987.2, dated May 23, 2018, 6 pages.
International Search Report for PCT International Application No. PCT/IB2018/059957, dated Apr. 9, 2019, 5 pages.
International Search Report for PCT International Application No. PCT/IB2018/059956, dated Feb. 12, 2019, 4 pages.
International Search Report for PCT International Application No. PCT/IB2018/059955, dated Feb. 5, 2019, 4 pages.

PROCESS FOR THE MANUFACTURING OF A 3-HALOPROPIONYL HALIDE IN A FLOW REACTOR

Cross Reference to Related Applications

This application is a national stage filing under 35 U.S.C. 371 of PCT/IB2018/059956, filed Dec. 12, 2018, which claims the benefit of European Application No. 17208982.3, filed Dec. 20, 2017, the disclosure of which is incorporated by reference in its/their entirety herein.

TECHNICAL FIELD

The present disclosure relates to the field of manufacturing acid halides, in particular acid chlorides, in flow reactors.

BACKGROUND

Halogenation, in particular chlorination, of organic acids to form organic acid chlorides can produce valuable intermediates as described in U.S. Pat. No. 2,013,988 (Meder et al.). The broad utility of acid halides, in particular acid chlorides, has drawn tremendous attention over the years. This class of compounds is important to facilitate numerous synthetic transformations owing to their high reactivity. Among this category of compounds, alpha, beta-unsaturated acid chlorides, in particular acryloyl chlorides and 3-chloropropionylchloride have received significant attention since the late $20^{th}$ century. These specific acid halides are highly reactive intermediates which can be used for the production of important acrylates and polymers with commercial applications in particular in adhesives, fine and specialty chemicals, absorbents, coating materials, and paints. Among the known organic acid halides, 3-chloropropionylchloride has recently emerged as an interesting building block with potential applications in particular for the manufacturing of polymers, pharmaceuticals, herbicides and fungicides. 3-halopropionylhalides, in particular 3-chloropropionylchloride, have been identified as a valuable replacement for acryloyl chlorides, due to their higher stability for example against auto-polymerization. There is therefore an increased interest in the manufacturing of 3-halopropionylhalides.

Due to their high reactivity and sensitivity towards hydrolysis, the manufacturing of 3-halopropionylhalides, on industrial scale is not always satisfactory. Moreover, the known processes for the selective halogenation of organic acids are highly exothermic, give mediocre yields and generally involve using hazardous chemical reagents, which then require taking additional and appropriate processing steps.

Processes to make 3-halopropionylhalides, in particular 3-chloropropionylchloride, include for example chlorination of beta-propiolactone, chlorination of acrylic acid as described for example in WO2005/092842 (Nozawa et al.), reaction of acrylic acid with methyldichloro phosphine, as described in U.S. Pat. No. 4,096,182 (Rupp et al.), and chlorination of 3-chloropropionic acid or reaction of carbon tetrachloride with propionyl chloride.

Recently, the so-called micro-reactor technology, also known as flow technology, has emerged as a powerful tool for carrying out organic chemical reactions, especially reactions involving hazardous chemicals. This technology has been documented in *Chem. Commun.*, 2011, 47, 6512-6535 (Charlotte Wiles and Paul Watts), and in Chem. Soc. Rev. 2016, vol 45, 4892-4928 (M. Movsisyan et al.). Flow reactor technology for the chlorination of acrylic acid to produce (meth)acryloylchlorides is described in U.S. Patent Application Publication No. 2010/0185013 A1 (Pinnow et al.) and in Chem Sus Chem 2016, 9, 1945-1952 (M. Movsisyan et al.).

The disclosed methods are not satisfactory for the manufacturing of specifically 3-halopropionylhalides, mainly due to a lack of selectivity and poor overall yields of 3-halopropionylhalides obtained.

Without contesting the technical advantages associated with the manufacturing processes known in the art, there is still a need for a process for the manufacturing of a 3-halopropionylhalide, which overcomes the above-described deficiencies.

Other advantages of the process of the disclosure will be apparent from the following description.

SUMMARY

According to one aspect, the present disclosure relates to a process for the manufacturing of a 3-halopropionylhalide, wherein the process comprises the steps of:
a) providing a flow reactor comprising a reaction chamber;
b) providing reactants comprising:
   i. acrylic acid;
   ii. a reaction co-agent selected from the group consisting of N,N-disubstituted amides; and
   iii. a halogenating agent; and
c) incorporating the reactants into the reaction chamber of the flow reactor, thereby forming a reaction product stream comprising a 3-halopropionylhalide;
wherein the molar ratio of acrylic acid to the halogenating agent is 1 to at least 0.8; wherein the temperature of the reaction chamber of the flow reactor is greater than 60° C.; and wherein the residence time of the reaction product stream comprising the 3-halopropionylhalide in the reaction chamber of the flow reactor is greater than 10 minutes.

DETAILED DESCRIPTION

According to one aspect, the present disclosure relates to a process for the manufacturing of a 3-halopropionylhalide, wherein the process comprises the steps of:
a) providing a flow reactor comprising a reaction chamber;
b) providing reactants comprising:
   i. acrylic acid;
   ii. a reaction co-agent selected from the group consisting of N,N-disubstituted amides; and
   iii. a halogenating agent; and
c) incorporating the reactants into the reaction chamber of the flow reactor, thereby forming a reaction product stream comprising a 3-halopropionylhalide; wherein the molar ratio of acrylic acid to the halogenating agent is 1 to at least 0.8; wherein the temperature of the reaction chamber of the flow reactor is greater than 60° C.; and wherein the residence time of the reaction product stream comprising the 3-halopropionylhalide in the reaction chamber of the flow reactor is greater than 10 minutes.

In the context of the present disclosure, it has been surprisingly found that a process as described above provides an efficient, simple, safe, versatile and selective method for the manufacturing of 3-halopropionylhalides, in particular 3-chloropropionylchloride.

Advantageously, the process of the present disclosure is a robust and production-efficient process, which can be performed in the absence of any solvent. The process of the present disclosure further provides excellent control of the reaction temperature profile (efficient thermal management), in particular through ensuring rapid and homogeneous mixing, as well as efficient transport of the starting material and intermediate reaction mixtures during the reaction process. As such, the process of the present disclosure allows using a broad scope of possible halogenating agents for the manufacturing of 3-halopropionylhalides, in particular 3-chloropropionylchloride.

In some other advantageous aspects, the process of the present disclosure is able to provide very high yield of reactive compounds having excellent purity and quality due to the selective halogenation, in particular chlorination, of acrylic acid on the olefinic unsaturation and the carboxylic acid group.

Without wishing to be bound by theory, it is believed that these excellent properties are due in particular to the specific combination of the use of a flow reactor, the use of specific reactants in particular a reaction co-agent selected from the group consisting of N,N-disubstituted amides, the use of the specific molar ratios as mentioned above, and to the specific reaction conditions as mentioned above in particular those conditions relating to the temperature of the reaction chamber of the flow reactor during the reaction and to the residence time of the reaction product stream comprising the 3-halopropionylhalide in the reaction chamber of the flow reactor.

Still without wishing to be bound by theory, it is further believed that the halogenating agent reacts particularly efficiently with the N,N-disubstituted amide thus providing a very efficient halogenating agent ensuring a significantly enhanced conversion of acrylic acid into acryloyl halide and into 3-halopropionylhalide in a second step. As such, the process of the present disclosure provides a highly efficient halogenation procedure, in particular chlorination procedure.

In the context of the present disclosure, the term "addition stream" is meant to refer to reactants (such as e.g. the acrylic acid, the reaction co-agent, the halogenating agent or the optional solvent) flowing from an entry location to the reaction chamber of the flow reactor.

The term "reaction chamber" is meant to refer to a region or area of the flow reactor where separate incoming addition streams are combined and contact one another. The reactants of the addition streams mix and chemically react with one another thereby forming a reaction product stream, where one or the other of the reactants may surround the other.

In the context of the present disclosure, the term "flow speed" is meant to refer to the speed (in ml/min) at which an addition stream is incorporated into the reaction chamber of the flow reactor.

The term "residence time" is meant to refer to the period of time the reaction product stream remains in the reaction chamber of the flow reactor from the moment the first addition stream and the second addition stream are incorporated and mixed into the reaction chamber of the flow reactor until the moment the reaction product stream exits the reaction chamber.

In the context of the present disclosure, the expression "molar ratio of compound X to compound Y" is meant to refer to the ratio of moles used of compound X relative to the moles used of compound Y. The calculation of the molar ratio of two compounds is well within the capabilities of those skilled in the art.

In the context of the present disclosure still, the expression "conversion rate of acrylic acid into a 3-halopropionylhalide" is meant to refer to the molar percentage of acrylic acid which is actually converted into the 3-halopropionylhalide, as determined by $^1$H NMR spectroscopy on the unpurified reaction mixture.

The process of the present disclosure comprises, as a first technical feature, the step of providing a flow reactor comprising a reaction chamber.

Flow reactors for use herein are not particularly limited. Any flow reactor comprising a reaction chamber comprising a reactive mixing chamber commonly known in the art may be used in the context of the present disclosure. Suitable flow reactors for use herein will be easily identified by those skilled in the art, in the light of the present description.

Exemplary flow reactors comprising a reaction chamber for use herein are described for example in WO2017/147040 (Dams et al.), U.S. Patent Application Publication No. 2011/0071307 A1 (Ishiyama et al.) and U.S. Patent Application Publication No. 2011/0087041 A1 (Ishiyama et al.). Moreover, flow reactors and technologies have been documented in *Chem. Commun.*, 2011, 47, 6512-6535 (C. Wiles and P. Watts).

Suitable flow reactors for use herein are commercially available, for example, under the trade designation IDEX 91 (ACHROM, Belgium) and LABTRIX START 1805-L-2 (Chemtrix BV, UK), the latter of which can be fitted with a glass microchip, such as those available under the trade designation TYPE 3223 (Chemtrix BV), which can function as the reaction chamber.

Alternative flow reactors for use herein may be built of PFA-tubing with an inner diameter of for example 0.50 mm and a total volume of for example 0.5 ml. Suitable PFA-tubing for use herein are available under the trade designation "IDEX 1512L" from Achrom, Belgium. These alternative flow reactors may be suitably connected to syringe pumps commercially available, for example, under the trade designation Fusion Touch or Fusion Classic from Chemtrix BV or Africa Reagent pumps from Syrris, delivering at least two reactant streams from at least two gas-tight syringes, available under the trade designation "Hamilton Syringe 10 ml 1000 series GASTIGHT" available from Hamilton, through PFA tubing with an inner diameter of 1.0 mm, available under the trade designation "IDEX 1507" from Achrom, Belgium, to the reaction chamber of the flow reactor.

In a typical aspect, the flow reactors for use herein will have various addition ports for adding reactants and additions streams to the reaction chamber of the flow reactor. In many cases, only two, three, or four addition ports are used for adding material to the reaction chamber. When there are unused addition ports, the unused addition ports will typically be plugged so as to prevent the intake of any unwanted substances from outside the reaction chamber. One or more of the addition ports can have a check valve to prevent backflow, but this is not needed in most cases because the pressure of the reactant stream through the addition port is usually sufficient to prevent backflow. The reaction chamber of the flow reactor will also typically have at least one exit port for a product stream to exit.

In a particular aspect, the flow reactor can be a microreactor, wherein the reaction chamber of the flow reactor for use herein has an internal volume of no greater than 5 ml, no greater than 1 ml, no greater than 800 microlitres, no greater than 600 microlitres, no greater than 500 microlitres, no greater than 400 microlitres, no greater than 300 microlitres, no greater than 250 microlitres, no greater than 200 microlitres, no greater than 150 microlitres, no greater than 100 microlitres, or even no greater than 50 microlitres.

In another particular aspect, the reaction chamber of the flow reactor has an internal volume of no greater than 500 ml, no greater than 400 ml, no greater than 300 ml, no greater than 200 ml, no greater than 150 ml, no greater than 100 ml, no greater than 80 ml, no greater than 60 ml, no greater than 40 ml, no greater than 20 ml, or even no greater than 10 ml.

The flow reactors for use herein typically have a reaction chamber that has a geometry for promoting mixing of the reactants added to the reaction chamber. In many cases, the mixing chamber can be designed to create a flowing plug of reactants such that back-mixing of materials in the flow reactor with materials later added to the flow reactor is mitigated. The reaction chamber can have any suitable geometry, such as a T-shape, star-shape, or circuitous tube shape.

In one particular aspect, the process of the present disclosure further comprises the steps of:
a) providing a first addition stream comprising acrylic acid and the reaction co-agent;
b) providing a second addition stream comprising the halogenating agent; and
c) incorporating the first addition stream and the second addition stream into the reaction chamber of the flow reactor, thereby forming a reaction product stream comprising a 3-halopropionylhalide.

In another particular aspect, the process of the present disclosure comprises the steps of:
a) providing a first addition stream comprising acrylic acid;
b) providing a second addition stream comprising the halogenating agent;
c) providing a third addition stream comprising the reaction co-agent; and
d) incorporating the first addition stream, the second addition stream and the third addition stream into the reaction chamber of the flow reactor, thereby forming a reaction product stream comprising a 3-halopropionylhalide.

As will be easily apparent to those skilled in the art, the flow reactor for use herein may comprise various addition ports for the incorporation of various reagent/reactant addition streams into the reaction chamber. The various reagent/reactant addition streams may be incorporated into the reaction chamber through distinct or common addition ports. Also, the various reactant addition streams may be incorporated into the reaction chamber simultaneously or at distinct addition times.

In an exemplary aspect, the flow reactor further comprises at least a first addition port, a second addition port, and optionally a third addition port, and the first addition stream is incorporated into the reaction chamber of the flow reactor through the first addition port, the second addition stream is incorporated through the second addition port, and the optional third addition stream is incorporated through the optional third addition port.

In one particular aspect of the process, the reactants, and in particular the first addition stream, the second addition stream, and the optional third addition stream are pre-mixed prior to incorporation into the reaction chamber of the flow reactor.

In another particular aspect of the process, the first addition stream and the third addition stream are pre-mixed prior to incorporation into the reaction chamber of the flow reactor thereby forming a combined addition stream, and the combined addition stream is then incorporated into the reaction chamber of the flow reactor, in particular simultaneously with the second addition stream.

According to a typical aspect of the process of the present disclosure, the first addition stream, the second addition stream, and the optional third addition stream are incorporated simultaneously into the reaction chamber of the flow reactor. Alternatively, the first addition stream, the second addition stream, and the optional third addition stream are incorporated into the reaction chamber of the flow reactor in successive steps.

In practice, the various reactant addition streams are incorporated and allowed to combine and contact one another to chemically react with one another in the reaction chamber of the flow reactor, thereby forming a reaction product stream comprising the 3-halopropionylhalide.

In one exemplary aspect of the process according to the disclosure, the first addition stream, the second addition stream, and the optional third addition stream are incorporated and combined into the reaction chamber of the flow reactor, thereby forming a reaction product stream comprising a 3-halopropionylhalide.

The temperature of the various reactants and addition streams for use herein are not particularly limited. The temperature of the reaction chamber of the flow reactor is typically selected such that the halogenation reaction proceeds in high yields within a suitable residence time. Suitable temperatures for use herein will be easily identified by those skilled in the art, in the light of the present description.

In an advantageous aspect of the process, the temperature of the reactants, and in particular the first addition stream, the second addition stream, and the optional third addition stream are such that the reactants, and in particular the first addition stream, the second addition stream, and the optional third addition stream are liquid prior to incorporation into the reaction chamber of the flow reactor. In an alternative aspect, the temperature of the reactants, and in particular the first addition stream, the second addition stream, and the optional third addition stream are such that the reactants, and in particular the first and second addition stream are at least flowable/pumpable through conventional addition pumps prior to incorporation into the reaction chamber of the flow reactor and without clogging or blocking the reaction chamber of the flow reactor.

According to a typical aspect of the process of the present disclosure, the temperature of the reactants and in particular of at least one of the first addition stream, the second addition stream, and the optional third addition stream is in range from 10° C. to 120° C., from 10° C. to 100° C., from 10° C. to 80° C., from 20° C. to 60° C., from 20° C. to 50° C. or even from 20° C. to 30° C., prior to incorporation into the reaction chamber of the flow reactor.

According to an advantageous aspect of the process, the temperature of the reaction chamber of the flow reactor is greater than 65° C., greater than 70° C., greater than 75° C., greater than 80° C., greater than 85° C., greater than 90° C., or even greater than 95° C., after incorporation of the reactants, and in particular the first addition stream, the second addition stream, and the optional third addition stream into the reaction chamber of the flow reactor.

According to another advantageous aspect of the process, the temperature of the reaction chamber of the flow reactor is no greater than 120° C., no greater than 110° C., no greater than 100° C., no greater than 90° C., no greater than 85° C., or even no greater than 80° C., after incorporation of the reactants, and in particular the first addition stream, the second addition stream, and the optional third addition stream into the reaction chamber of the flow reactor.

In a preferred aspect, the temperature of the reaction chamber of the flow reactor is in a range from 60° C. to 120° C., from 60° C. to 100° C., from 60° C. to 95° C., from 60° C. to 90° C., from 65° C. to 85° C., from 70° C. to 85° C., from 75° C. to 85° C., or even from 75° C. to 80° C., after incorporation of the reactants, and in particular the first addition stream, the second addition stream, and the optional third addition stream into the reaction chamber of the flow reactor.

In a more preferred aspect, the temperature of the reaction chamber of the flow reactor is of about 80° C., after incorporation of the reactants, and in particular the first addition stream, the second addition stream, and the optional third addition stream into the reaction chamber of the flow reactor.

The various reactants and addition streams may be incorporated into the reaction chamber of the flow reactor using any means commonly known in the art. In a particular aspect, the reactants, the first addition stream, the second addition stream, and the optional third addition stream are incorporated into the reaction chamber by using suitable (high) pressure pumps such as rotary pumps, screw pumps, plunger plumps, gear pumps, peristaltic pumps, syringe pumps or piston pumps.

The flow speed of the various reactants and addition streams for use herein is not particularly limited. Suitable flow speeds for use herein will be easily identified by those skilled in the art, in the light of the present description. In particular, the flow speed of the various addition streams for use herein may be appropriately chosen such that the molar ratios between the different reactants is according to the process and maintained constant throughout the process.

In an advantageous aspect of the process, the reactants, the first addition stream, the second addition stream, and the optional third addition stream are incorporated into the reaction chamber of the flow reactor each at a flow speed in a range from 0.005 ml/min to 500 ml/min, from 0.005 ml/min to 300 ml/min, from 0.01 ml/min to 200 ml/min, from 0.01 ml/min to 100 ml/min, 0.01 ml/min to 80 ml/min, 0.05 ml/min to 60 ml/min, 0.08 ml/min to 50 ml/min, from 0.1 ml/min to 40 ml/min, from 0.1 ml/min to 20 ml/min, or even from 0.1 ml/min to 10 ml/min.

In another advantageous aspect, the first addition stream is incorporated into the reaction chamber of the flow reactor at a flow speed in a range from 0.01 ml/min to 50 ml/min, from 0.01 ml/min to 30 ml/min, from 0.01 ml/min to 10 ml/min, from 0.01 ml/min to 5 ml/min, from 0.05 ml/min to 4 ml/min, from 0.05 ml/min to 2.0 ml/min, from 0.10 ml/min to 1.5 ml/min, from 0.20 ml/min to 1.0 ml/min, or even from 0.30 ml/min to 0.40 ml/min.

In still another advantageous aspect, the second addition stream is incorporated into the reaction chamber of the flow reactor at a flow speed in a range from 0.01 ml/min to 50 ml/min, from 0.01 ml/min to 30 ml/min, from 0.01 ml/min to 10 ml/min, from 0.01 ml/min to 5 ml/min, from 0.01 ml/min to 2 ml/min, from 0.05 ml/min to 1.5 ml/min, from 0.08 ml/min to 1.0 ml/min, from 0.10 ml/min to 0.80 ml/min, from 0.10 ml/min to 0.50 ml/min, or even from 0.15 ml/min to 0.20 ml/min.

In yet another advantageous aspect, the first addition stream and the third addition stream are pre-mixed prior to incorporation into the reaction chamber of the flow reactor thereby forming a combined addition stream, wherein the combined addition stream is then incorporated into the reaction chamber of the flow reactor, in particular simultaneously with the second addition stream, and wherein the combined addition stream is incorporated into the reaction chamber of the flow reactor at a flow speed in a range from 0.01 ml/min to 50 ml/min, from 0.01 ml/min to 30 ml/min, from 0.01 ml/min to 10 ml/min, from 0.05 ml/min to 5 ml/min, from 0.10 ml/min to 3.0 ml/min, from 0.10 ml/min to 1.5 ml/min, from 0.30 ml/min to 1.0 ml/min, or even from 0.40 ml/min to 0.60 ml/min.

The residence time of the reaction product stream comprising the 3-halopropionylhalide in the reaction chamber of the flow reactor for use herein is not particularly limited as long as it is greater than 10 minutes. Suitable residence times for use herein will be easily identified by those skilled in the art, in the light of the present description.

According to a beneficial aspect of the process of the present disclosure, the residence time of the reaction product stream comprising the 3-halopropionylhalide in the reaction chamber of the flow reactor is greater than 12 minutes, greater than 15 minutes, greater than 17 minutes, greater than 20 minutes, greater than 22 minutes, greater than 25 minutes, greater than 30 minutes, greater than 40 minutes, greater than 50 minutes, or even greater than 55 minutes.

In another beneficial aspect of the process, the residence time of reaction product stream comprising the 3-halopropionylhalide in the reaction chamber of the flow reactor is no greater than 60 minutes, no greater than 55 minutes, no greater than 50 minutes, no greater than 45 minutes, no greater than 40 minutes, no greater than 35 minutes, no greater than 30 minutes, or even no greater than 25 minutes.

In still another beneficial aspect of the process, the residence time of the reaction product stream comprising the 3-halopropionylhalide in the reaction chamber of the flow reactor is in a range from 15 to 60 minutes, from 15 to 55 minutes, from 15 to 50 minutes, from 15 to 45 minutes, from 15 to 40 minutes, from 15 to 35 minutes, from 15 to 30 minutes, or even from 20 to 30 minutes.

In yet a further beneficial aspect of the process, the residence time of the reaction product stream comprising the 3-halopropionylhalide in the reaction chamber of the flow reactor is about 25 minutes or about 45 minutes The reactants, and in particular the first addition stream for use in the process according to the present disclosure, comprise acrylic acid. Acrylic acid is readily and commercially available for example from Sigma-Aldrich, Belgium.

The reactants, and in particular the first addition stream or the optional third addition stream for use in the process according to the present disclosure, comprise a reaction co-agent selected from the group consisting of N,N-disubstituted amides. N,N-disubstituted amides for use herein are not particularly limited. Any N,N-disubstituted amide commonly known in the art may be used in the context of the present disclosure. Suitable N,N-disubstituted amides for use herein will be easily identified by those skilled in the art, in the light of the present description.

According to a typical aspect of the process, the reaction co-agent for use herein is selected from the group consisting of linear N,N-disubstituted amides, cyclic N,N-disubstituted amides, heterocyclic N,N-disubstituted amides, and any combinations or mixtures thereof.

According to an advantageous aspect, the reaction co-agent is selected from the group consisting of N,N-disubstituted heterocyclic amides and N,N-dialkyl amides, wherein the alkyl group is preferably selected from the group of methyl, ethyl, propyl and butyl.

In a beneficial aspect, the reaction co-agent for use in the process of the present disclosure is selected from the group consisting of N,N-dialkyl formamides and N,N-dialkyl acetamides, wherein the alkyl group is preferably selected from the group of methyl, ethyl, propyl and butyl.

In another beneficial aspect, the reaction co-agent for use herein is selected from the group consisting of N,N-disubstituted heterocyclic amides, for example N-formyl morpholine.

In still another beneficial aspect, the reaction co-agent is selected from the group consisting of N,N-dimethyl formamide, N,N-diethyl formamide, N,N-dimethyl acetamide, N-formyl morpholine, and any combinations or mixtures thereof.

According to a particularly beneficial aspect, the reaction co-agent is selected from the group consisting of N,N-dimethyl formamide, N,N-diethyl formamide, N-formyl morpholine, and any combinations or mixtures thereof.

According to a particularly preferred aspect, the reaction co-agent for use in the process of the present disclosure is selected to be N,N-dimethyl formamide.

The reactants, and in particular the second addition stream for use in the process according to the present disclosure, comprise a halogenating agent. Halogenating agents for use herein are not particularly limited. Any halogenating agent commonly known in the art may be used in the context of the present disclosure. Suitable halogenating agents for use herein will be easily identified by those skilled in the art, in the light of the present description.

According to an advantageous aspect of the process, the halogenating agent is a chlorinating agent, preferably selected from the group consisting of thionyl chloride, phosphoryl chloride, oxalyl chloride, phosgene, triphosgene, and any mixtures thereof.

According to another advantageous aspect of the process, the halogenating agent is a brominating agent, preferably selected from the group consisting of thionyl bromide, phosphoryl bromide, and any mixtures thereof.

According to a more advantageous aspect of the process, the halogenating agent is selected from the group consisting of thionyl chloride, phosphoryl chloride, oxalyl chloride, and any mixtures thereof.

In a preferred aspect, the halogenating agent for use in the process of the disclosure is selected from the group consisting of thionyl chloride, phosphoryl chloride, and any mixtures thereof.

In a particularly preferred aspect, the halogenating agent for use in the process of the disclosure is selected to be thionyl chloride.

According to one advantageous aspect of the process of the present disclosure, the molar ratio of acrylic acid to the halogenating agent is 1 to at least 0.9; 1 to at least 1; 1 to at least 1.02; 1 to at least 1.05; 1 to at least 1.10; 1 to at least 1.15; 1 to at least 1.20; 1 to at least 1.30; 1 to at least 1.40; 1 to at least 1.50; 1 to at least 1.60; 1 to at least 1.70; 1 to at least 1.80; or even 1 to at least 2.0.

According to another advantageous aspect of the process of the present disclosure, the molar ratio of acrylic acid to the halogenating agent is no greater than 1 to 2; no greater than 1 to 1.8; no greater than 1 to 1.6; no greater than 1 to 1.5; no greater than 1 to 1.4; no greater than 1 to 1.3; or even no greater than 1 to 1.2.

According to still another advantageous aspect of the process of the present disclosure, the molar ratio of acrylic acid to the halogenating agent is in a range between 1 to 0.8 and 1 to 2.0, between 1 to 0.8 and 1 to 1.8, between 1 to 0.9 and 1 to 1.60, between 1 to 1 and 1 to 1.5, between 1 to 1 and 1 to 1.4, between 1 to 1 and 1 to 1.30, or even between 1 to 1 and 1 to 1.2.

According to a preferred aspect of the process of the present disclosure, the molar ratio of acrylic acid to the halogenating agent is about 1 to 1, in particular 1 to 1.1.

In another advantageous aspect of the process, the molar ratio of acrylic acid to the reaction co-agent is 1 to at least 0.1; 1 to at least 0.2; 1 to at least 0.3; 1 to at least 0.4; 1 to at least 0.5; 1 to at least 0.6; 1 to at least 0.7; 1 to at least 0.8; 1 to at least 0.9; 1 to at least 1; 1 to at least 1.02; 1 to at least 1.05; 1 to at least 1.1; 1 to at least 1.15; 1 to at least 1.2; 1 to at least 1.3; 1 to at least 1.4; 1 to at least 1.5; 1 to at least 1.6; 1 to at least 1.7; 1 to at least 1.8; or even 1 to at least 2.

In still another advantageous aspect of the process, the molar ratio of acrylic acid to the reaction co-agent is in a range between 1 to 0.1 and 1 to 2, between 1 to 0.1 and 1 to 1.8, between 1 to 0.1 and 1 to 1.7, between 1 to 0.1 and 1 to 1.6.

In a preferred aspect of the process of the present disclosure, the molar ratio of acrylic acid to the reaction co-agent is about 1 to 0.1, about 1 to 0.5, or even about 1 to 1.5.

In an advantageous aspect, the process according to the present disclosure is performed in absence of any solvents. However, in an alternative aspect, the process of the present disclosure may comprise the optional step of incorporating at least one organic solvent into the reaction chamber of the flow reactor.

This additional and optional step may be in particular advantageous in those situations where neither of the reactants, the first addition stream, the second addition stream or third addition stream is in a physical state suitable for it to be appropriately incorporated into the reaction chamber of the flow reactor. This is in particular the case when either of the reactants, the first addition stream, the second addition stream or third addition stream is neither liquid nor flowable/pumpable through conventional flow reactor addition pumps (including high pressure pumps) prior to incorporation into the reaction chamber of the flow reactor, even when subjected to a heating step. In other aspects, the use of an optional solvent may be advantageous to ensure optimized thermal management of the reactive process in the reaction chamber of the flow reactor or to reduce the viscosity of the reaction product formed.

Organic solvents for use herein are not particularly limited, as long as the organic solvent is unable to react with any of the reactants. Suitable organic solvents for use herein will be easily identified by those skilled in the art, in the light of the present description.

According to a typical aspect of the process, the at least one organic solvent is incorporated as part of the first addition stream and/or the second addition stream and/or the third addition stream, together with acrylic acid and/or the halogenating agent and/or the reaction co-agent.

In an exemplary aspect, the step of incorporating acrylic acid and/or the halogenating agent and/or the reaction co-agent into the reaction chamber of the flow reactor comprises incorporating a solution of acrylic acid and/or the halogenating agent and/or the reaction co-agent in the at least one organic solvent into the reaction chamber of the flow reactor.

According to one advantageous aspect of the process according to the present disclosure, the at least one organic solvent comprises one or more of dichloromethane, methyl ethyl ketone, heptane, cyclohexane, toluene, ethoxyethane, benzene, trichloro methane, or methyl isobutyl ketone.

According to another advantageous aspect of the process, the at least one organic solvent for use herein comprises dichloromethane, heptane, cyclohexane or toluene.

In a typical aspect of the process, the at least one organic solvent is incorporated into the reaction chamber of the flow reactor in an amount sufficient to substantially dissolve the acrylic acid and/or the halogenating agent and/or the reaction co-agent.

In another typical aspect of the process, the first addition stream comprising acrylic acid, the reaction co-agent and optionally the at least one organic solvent, is incorporated into the reaction chamber of the flow reactor through the first addition port.

In one exemplary execution of the process, the first addition stream comprising acrylic acid is incorporated into the reaction chamber of the flow reactor through the first addition port, the second addition stream comprising the halogenating agent is incorporated into the reaction chamber of the flow reactor through the second addition port, and the third addition stream comprising the reaction co-agent and optionally the at least one organic solvent is incorporated into the reaction chamber of the flow reactor through the third addition port.

In an alternative execution of the process, the reaction chamber of the flow reactor further comprises a fourth addition port, and wherein the optional at least one organic solvent is incorporated through the fourth addition port.

According to an alternative aspect of the present disclosure, the process for the manufacturing of a 3-halopropionylhalide may be performed solventless.

In one advantageous aspect, the reaction product stream is substantially free of solvents, in particular substantially free of organic solvents.

In one typical aspect of the present process, the first addition stream and/or the second addition stream and/or the optional third addition stream is free of solvents. In a particular aspect, all the addition streams are substantially free of solvents, in particular organic solvents.

As will be apparent to those skilled in the art, the reactants and the reaction product streams for use in the present process may comprise optional ingredients commonly known in the art for similar chemical reactions.

According to one advantageous aspect of the process of the disclosure, the reactants comprise polymerization inhibitors, in particular polymerization inhibitors selected from the group of phenothiazines and hydroquinones, in particular hydroquinone monomethyl ethers and hydroquinone methyl esters. In particular, the reactants may comprise polymerization inhibitors specifically for acrylic acid.

According to an advantageous aspect of the process of the present disclosure, the reaction product stream comprises the 3-halopropionylhalide in an amount of at least 55 wt %, at least 60 wt %, at least 65 wt %, at least 70 wt %, at least 75 wt %, at least 80 wt %, at least 85 wt %, at least 90 wt %, at least 95 wt %, or even at least 97 wt % based on the total weight of the 3-halopropionylhalide, acrylic acid, and the organic by-products in the reaction product stream.

The weights of the various components of the product stream can be measured by any suitable means, for example, by gas chromatography or NMR-spectroscopy. When gas chromatography is used, the compounds in the product stream can be identified by comparing their residence time to that of standards on the same column. The areas for the peaks can be calculated using standard software, or even manually, and then converted into concentration by using calibration curves. The calibration curves can be established by standard samples having known concentrations of the compounds. Other suitable means of determining the wt % of the various components of the product stream include, liquid chromatography, such as HPLC, and mass spectrometry.

According to another advantageous aspect of the process of the present disclosure, the conversion rate of acrylic acid into the 3-halopropionylhalide is of at least 55 mol %, at least 60 mol %, at least 65 mol %, at least 70 mol %, at least 75 mol %, at least 80 mol %, at least 85 mol %, at least 90 mol %, at least 95 mol %, or even at least 97 mol % based on the molar equivalent of acrylic acid, and when determined by $^1$H NMR spectroscopy.

The process of the present disclosure may comprise the optional step of applying pressure to the reaction product stream in the reaction chamber by installing for example a back-pressure regulator at the end of the reaction chamber. The back-pressure regulator is a device such as a control valve that reduces the input pressure of a fluid to a desired value at its output. The back-pressure regulator allows to maintain a pressure in the reaction chamber in order to for example speed up the reaction or increase its yield. Suitable back-pressure regulators for use herein are for example commercially available under the trade designation BPR cartridge "IDEX P-761" or "IDEX P-763", from Achrom Belgium.

In a beneficial aspect of the present disclosure, a pressure ranging from 0 to 10 bar, from 1 to bar, from 1 to 8 bar, from 1.5 to 8 bar, from 1.5 to 6 bar, from 2 to 6 bar, from 2 to 5 bar, from 2 to 4 bar, from 2 to 3 bar, or even from 2.5 to 3 bar.

The optional step of applying a pressure to the reaction product stream in the reaction chamber is particularly beneficial when thionyl chloride is used as halogenating agent.

According to one beneficial aspect of the present disclosure, the process as described herein may be performed as a continuous process.

Item 1 is a process for the manufacturing of a 3-halopropionylhalide, wherein the process comprises the steps of:
a) providing a flow reactor comprising a reaction chamber;
b) providing reactants comprising:
  i. acrylic acid;
  ii. a reaction co-agent selected from the group consisting of N,N-disubstituted amides; and
  iii. a halogenating agent; and
c) incorporating the reactants into the reaction chamber of the flow reactor, thereby forming a reaction product stream comprising a 3-halopropionylhalide; wherein the molar ratio of acrylic acid to the halogenating agent is 1 to at least 0.8; wherein the temperature of the reaction chamber of the flow reactor is greater than 60° C.; and wherein the residence time of the reaction product stream comprising the 3-halopropionylhalide in the reaction chamber of the flow reactor is greater than 10 minutes.

Item 2 is a process according to item 1, wherein the process comprises the steps of:
a) providing a first addition stream comprising acrylic acid and the reaction co-agent;
b) providing a second addition stream comprising the halogenating agent; and
c) incorporating the first addition stream and the second addition stream into the reaction chamber of the flow reactor, thereby forming a reaction product stream comprising a 3-halopropionylhalide.

Item 3 is a process according to item 1, wherein the process comprises the steps of:
a) providing a first addition stream comprising acrylic acid;
b) providing a second addition stream comprising the halogenating agent;

c) providing a third addition stream comprising the reaction co-agent; and d) incorporating the first addition stream, the second addition stream and the third addition stream into the reaction chamber of the flow reactor, thereby forming a reaction product stream comprising a 3-halopropionylhalide.

Item 4 is a process according to item 2 or 3, wherein the flow reactor further comprises at least a first addition port, a second addition port, and optionally a third addition port, and wherein the first addition stream is incorporated into the reaction chamber of the flow reactor through the first addition port, the second addition stream is incorporated through the second addition port, and the optional third addition stream is incorporated through the optional third addition port.

Item 5 is a process according to any of the preceding items, wherein the reactants, and in particular the first addition stream, the second addition stream, and the optional third addition stream are pre-mixed prior to incorporation into the reaction chamber of the flow reactor.

Item 6 is a process according to item 5, wherein the first addition stream and the third addition stream are pre-mixed prior to incorporation into the reaction chamber of the flow reactor thereby forming a combined addition stream, and wherein the combined addition stream is then incorporated into the reaction chamber of the flow reactor, in particular simultaneously with the second addition stream.

Item 7 is a process according to any of the preceding items, wherein the reactants, and in particular the first addition stream, the second addition stream, and the optional third addition stream are incorporated simultaneously into the reaction chamber of the flow reactor.

Item 8 is a process according to any of the preceding items, wherein the reactants, and in particular the first addition stream, the second addition stream, and the optional third addition stream are incorporated into the reaction chamber of the flow reactor in successive steps.

Item 9 is a process according to any of the preceding items, wherein the reactants, and in particular the first addition stream, the second addition stream, and the optional third addition stream are incorporated and combined into the reaction chamber of the flow reactor, thereby forming a reaction product stream comprising a 3-halopropionylhalide.

Item 10 is a process according to any of the preceding items, wherein the first addition stream, the second addition stream, and the optional third addition stream are incorporated into the reaction chamber of the flow reactor each at a flow speed in a range from 0.005 ml/min to 500 ml/min, from 0.005 ml/min to 300 ml/min, from 0.01 ml/min to 200 ml/min, from 0.01 ml/min to 100 ml/min, 0.01 ml/min to 80 ml/min, 0.05 ml/min to 60 ml/min, 0.08 ml/min to 50 ml/min, from 0.1 ml/min to 40 ml/min, from 0.1 ml/min to 20 ml/min, or even from 0.1 ml/min to 10 ml/min.

Item 11 is a process according to any of the preceding items, wherein the first addition stream is incorporated into the reaction chamber of the flow reactor at a flow speed in a range from 0.01 ml/min to 50 ml/min, from 0.01 ml/min to 30 ml/min, from 0.01 ml/min to 10 ml/min, from 0.01 ml/min to 5 ml/min, from 0.05 ml/min to 4 ml/min, from 0.05 ml/min to 2.0 ml/min, from 0.10 ml/min to 1.5 ml/min, from 0.20 ml/min to 1.0 ml/min, or even from 0.30 ml/min to 0.40 ml/min.

Item 12 is a process according to any of the preceding items, wherein the second addition stream is incorporated into the reaction chamber of the flow reactor at a flow speed in a range from 0.01 ml/min to 50 ml/min, from 0.01 ml/min to 30 ml/min, from 0.01 ml/min to 10 ml/min, from 0.01 ml/min to 5 ml/min, from 0.01 ml/min to 2 ml/min, from 0.05 ml/min to 1.5 ml/min, from 0.08 ml/min to 1.0 ml/min, from 0.10 ml/min to 0.80 ml/min, from 0.10 ml/min to 0.50 ml/min, or even from 0.15 ml/min to 0.20 ml/min.

Item 13 is a process according to any of the preceding items, wherein the first addition stream and the third addition stream are pre-mixed prior to incorporation into the reaction chamber of the flow reactor thereby forming a combined addition stream, wherein the combined addition stream is then incorporated into the reaction chamber of the flow reactor, in particular simultaneously with the second addition stream, and wherein the combined addition stream is incorporated into the reaction chamber of the flow reactor at a flow speed in a range from 0.01 ml/min to 50 ml/min, from 0.01 ml/min to 30 ml/min, from 0.01 ml/min to 10 ml/min, from 0.05 ml/min to 5 ml/min, from 0.10 ml/min to 3.0 ml/min, from 0.10 ml/min to 1.5 ml/min, from 0.30 ml/min to 1.0 ml/min, or even from 0.40 ml/min to 0.60 ml/min.

Item 14 is a process according to any of the preceding items, wherein the temperature of the reactants, and in particular he first addition stream, the second addition stream, and the optional third addition stream is such that the first addition stream, the second addition stream, and the optional third addition stream are liquid prior to incorporation into the reaction chamber of the flow reactor.

Item 15 is a process according to any of the preceding items, wherein the temperature of the reaction chamber of the flow reactor is greater than 65° C., greater than 70° C., greater than 75° C., greater than 80° C., greater than 85° C., greater than 90° C., or even greater than 95° C., after incorporation of the reactants, and in particular the first addition stream, the second addition stream, and the optional third addition stream into the reaction chamber of the flow reactor.

Item 16 is a process according to any of the preceding items, wherein the temperature of the reaction chamber of the flow reactor is no greater than 120° C., no greater than 110° C., no greater than 100° C., no greater than 90° C., no greater than 85° C., or even no greater than 80° C., after incorporation of the reactants, and in particular the first addition stream, the second addition stream, and the optional third addition stream into the reaction chamber of the flow reactor.

Item 17 is a process according to any of the preceding items, wherein the temperature of the reaction chamber of the flow reactor is in a range from 60° C. to 120° C., from 60° C. to 100° C., from 60° C. to 95° C., from 60° C. to 90° C., from 65° C. to 85° C., from 70° C. to 85° C., from 75° C. to 85° C., or even from 75° C. to 80° C., after incorporation of the reactants, and in particular the first addition stream, the second addition stream, and the optional third addition stream into the reaction chamber of the flow reactor.

Item 18 is a process according to any of the preceding items, wherein the temperature of the reaction chamber of the flow reactor is of about 80° C., after incorporation of the reactants, and in particular the first addition stream, the second addition stream, and the optional third addition stream into the reaction chamber of the flow reactor.

Item 19 is a process according to any of the preceding items, wherein the temperature of the reactants and in particular of at least one of the first addition stream, the second addition stream, and the optional third addition stream is in range from 10° C. to 120° C., from 10° C. to 100° C., from 10° C. to 80° C., from 20° C. to 60° C., from 20° C. to 50° C. or even from 20° C. to 30° C. prior to incorporation into the reaction chamber of the flow reactor.

Item 20 is a process according to any of the preceding items, wherein the flow reactor is temperature controlled during the process.

Item 21 is a process according to any of the preceding items, wherein the reaction chamber of the flow reactor is temperature controlled during the process.

Item 22 is a process according to any of the preceding items, wherein the residence time of the reaction product stream comprising the 3-halopropionylhalide in the reaction chamber of the flow reactor is greater than 12 minutes, greater than 15 minutes, greater than 17 minutes, greater than 20 minutes, greater than 22 minutes, greater than 25 minutes, greater than 30 minutes, greater than 40 minutes, greater than 50 minutes, or even greater than 55 minutes.

Item 23 is a process according to any of the preceding items, wherein the residence time of reaction product stream comprising the 3-halopropionylhalide in the reaction chamber of the flow reactor is no greater than 60 minutes, no greater than 55 minutes, no greater than 50 minutes, no greater than 45 minutes, no greater than 40 minutes, no greater than 35 minutes, no greater than 30 minutes, or even no greater than 25 minutes.

Item 24 is a process according to any of the preceding items, wherein the residence time of the reaction product stream comprising the 3-halopropionylhalide in the reaction chamber of the flow reactor is in a range from 15 to 60 minutes, from 15 to 55 minutes, from 15 to 50 minutes, from 15 to 45 minutes, from 15 to 40 minutes, from 15 to 35 minutes, from 15 to 30 minutes, or even from 20 to 30 minutes.

Item 25 is a process according to any of the preceding items, wherein the residence time of the reaction product stream comprising the 3-halopropionylhalide in the reaction chamber of the flow reactor is about 25 minutes or about 45 minutes.

Item 26 is a process according to any of the preceding items, wherein the reaction chamber of the flow reactor has an internal volume of no greater than 5 ml, no greater than 1 ml, no greater than 800 microlitres, no greater than 600 microlitres, no greater than 500 microlitres, no greater than 400 microlitres, no greater than 300 microlitres, no greater than 250 microlitres, no greater than 200 microlitres, no greater than 150 microlitres, no greater than 100 microlitres, or even no greater than 50 microlitres.

Item 27 is a process according to any of items 1 to 25, wherein the reaction chamber of the flow reactor has an internal volume of no greater than 500 ml, no greater than 400 ml, no greater than 300 ml, no greater than 200 ml, no greater than 150 ml, no greater than 100 ml, no greater than 80 ml, no greater than 60 ml, no greater than 40 ml, no greater than 20 ml, or even no greater than 10 ml.

Item 28 is a process according to any of the preceding items, wherein the reaction co-agent is selected from the group consisting of linear N,N-disubstituted amides, cyclic N,N-disubstituted amides, heterocyclic N,N-disubstituted amides, and any combinations or mixtures thereof.

Item 29 is a process according to any of the preceding items, wherein the N,N-disubstituted amides are selected from the group consisting of N,N-disubstituted heterocyclic amides and N,N-dialkyl amides, wherein the alkyl group is preferably selected from the group of methyl, ethyl, propyl and butyl.

Item 30 is a process according to any of the preceding items, wherein the reaction co-agent is selected from the group consisting of N,N-dialkyl formamides and N,N-dialkyl acetamides, wherein the alkyl group is preferably selected from the group of methyl, ethyl, propyl and butyl.

Item 31 is a process according to any of items 1 to 30, wherein the N,N-disubstituted amides are selected from the group consisting of N,N-disubstituted heterocyclic amides.

Item 32 is a process according to any of the preceding items, wherein the reaction co-agent is selected from the group consisting of N,N-dimethyl formamide, N,N-diethyl formamide, N,N-dimethyl acetamide, N-formyl morpholine, and any combinations or mixtures thereof.

Item 33 is a process according to any of the preceding items, wherein the reaction co-agent is selected from the group consisting of N,N-dimethyl formamide, N,N-diethyl formamide, N-formyl morpholine, and any combinations or mixtures thereof.

Item 34 is a process according to any of the preceding items, wherein the reaction co-agent is selected to be N,N-dimethyl formamide.

Item 35 is a process according to any of the preceding items, wherein the halogenating agent is selected from the group of chlorinating agents or brominating agents, preferably chlorinating agents.

Item 36 is a process according to any of the preceding items, wherein the halogenating agent is a chlorinating agent preferably selected from the group consisting of thionyl chloride, phosphoryl chloride, oxalyl chloride, phosgene, triphosgene, and any mixtures thereof.

Item 37 is a process according to any of items 1 to 35, wherein the halogenating agent is a brominating agent preferably selected from the group consisting of thionyl bromide, phosphoryl bromide, and any mixtures thereof.

Item 38 is a process according to any of the preceding items, wherein the halogenating agent is selected from the group consisting of thionyl chloride, phosphoryl chloride, oxalyl chloride, phosgene, triphosgene, thionyl bromide, phosphoryl bromide, and any mixtures thereof.

Item 39 is a process according to any of the preceding items, wherein the halogenating agent is selected from the group consisting of thionyl chloride, phosphoryl chloride, oxalyl chloride, phosgene, and any mixtures thereof.

Item 40 is a process according to any of the preceding items, wherein the halogenating agent is selected from the group consisting of thionyl chloride, phosphoryl chloride, and any mixtures thereof.

Item 41 is a process according to any of the preceding items, wherein the halogenating agent is selected to be thionyl chloride.

Item 42 is a process according to any of the preceding items, wherein the molar ratio of acrylic acid to the halogenating agent is 1 to at least 0.9; 1 to at least 1; 1 to at least 1.02; 1 to at least 1.05; 1 to at least 1.10; 1 to at least 1.15; 1 to at least 1.20; 1 to at least 1.30; 1 to at least 1.40; 1 to at least 1.50; 1 to at least 1.60; 1 to at least 1.70; 1 to at least 1.80; or even 1 to at least 2.0.

Item 43 is a process according to any of the preceding items, wherein the molar ratio of acrylic acid to the halogenating agent is no greater than 1 to 2; no greater than 1 to 1.8; no greater than 1 to 1.6; no greater than 1 to 1.5; no greater than 1 to 1.4; no greater than 1 to 1.3; or even no greater than 1 to 1.2.

Item 44 is a process according to any of the preceding items, wherein the molar ratio of acrylic acid to the halogenating agent is in a range between 1 to 0.8 and 1 to 2.0, between 1 to 0.8 and 1 to 1.8, between 1 to 0.9 and 1 to 1.60, between 1 to 1 and 1 to 1.5, between 1 to 1 and 1 to 1.4, between 1 to 1 and 1 to 1.30, or even between 1 to 1 and 1 to 1.2.

Item 45 is a process according to any of the preceding items, wherein the molar ratio of acrylic acid to the halogenating agent is about 1 to 1, in particular 1 to 1.1.

Item 46 is a process according to any of the preceding items, wherein the molar ratio of acrylic acid to the reaction co-agent is 1 to at least 0.1; 1 to at least 0.2; 1 to at least 0.3; 1 to at least 0.4; 1 to at least 0.5; 1 to at least 0.6; 1 to at least 0.7; 1 to at least 0.8; 1 to at least 0.9; 1 to at least 1; 1 to at least 1.02; 1 to at least 1.05; 1 to at least 1.1; 1 to at least 1.15; 1 to at least 1.2; 1 to at least 1.3; 1 to at least 1.4; 1 to at least 1.5; 1 to at least 1.6; 1 to at least 1.7; 1 to at least 1.8; or even 1 to at least 2.

Item 47 is a process according to any of the preceding items, wherein the molar ratio of acrylic acid to the reaction co-agent is in a range between 1 to 0.1 and 1 to 2, between 1 to 0.1 and 1 to 1.8, between 1 to 0.1 and 1 to 1.7, between 1 to 0.1 and 1 to 1.6.

Item 48 is a process according to any of the preceding items, wherein the molar ratio of acrylic acid to the reaction co-agent is about 1 to 0.1, about 1 to 0.5, or even about 1 to 1.5.

Item 49 is a process according to any of the preceding items, wherein the reaction product stream comprises the 3-halopropionylhalide in an amount of at least 55 wt %, at least 60 wt %, at least 65 wt %, at least 70 wt %, at least 75 wt %, at least 80 wt %, at least 85 wt %, at least 90 wt %, at least 95 wt %, or even at least 97 wt % based on the total weight of 3-chloropropionylhalide, acrylic acid, and the organic by-products in the reaction product stream.

Item 50 is a process according to any of the preceding items, wherein the conversion rate of acrylic acid into the 3-halopropionylhalide is of at least 55 mol %, at least 60 mol %, at least 65 mol %, at least 70 mol %, at least 75 mol %, at least 80 mol %, at least 85 mol %, at least 90 mol %, at least 95 mol %, or even at least 97 mol % based on the molar equivalent of acrylic acid, and when determined by $^1$H NMR spectroscopy.

Item 51 is a process according to any of the preceding items, wherein the 3-halopropionylhalide is 3-chloropropionylchloride or 3-bromopropionylbromide, preferably 3-chloropropionylchloride.

Item 52 is a process according to any of the preceding items, which further comprises the optional step of incorporating at least one organic solvent into the reaction chamber of the flow reactor.

Item 53 is a process according to item 48, wherein the at least one organic solvent is incorporated as part of the first addition stream and/or the second addition stream and/or the third addition stream, together with acrylic acid and/or the halogenating agent the reaction co-agent.

Item 54 is a process according to item 52, wherein the step of incorporating acrylic and/or the halogenating agent and/or the reaction co-agent into the reaction chamber of the flow reactor comprises incorporating a solution of acrylic acid and/or the halogenating agent and/or the reaction co-agent in the at least one organic solvent into the reaction chamber of the flow reactor.

Item 55 is a process according to any of items 52 to 54, wherein the at least one organic solvent comprises one or more of dichloromethane, methyl ethyl ketone, heptane, cyclohexane, toluene, ethoxyethane, benzene, trichloro methane, or methyl isobutyl ketone.

Item 56 is a process according to any of items 52 to 55, wherein the at least one organic solvent comprises dichloromethane, heptane, cyclohexane or toluene.

Item 57 is a process according to any of items 52 to 56, wherein the at least one organic solvent is incorporated into the reaction chamber of the flow reactor in an amount sufficient to substantially dissolve the acrylic acid and/or the halogenating agent and/or the reaction co-agent.

Item 58 is a method according to any of items 52 to 57, wherein the first addition stream comprising acrylic acid, the reaction co-agent and optionally the at least one organic solvent, is incorporated into the reaction chamber of the flow reactor through the first addition port.

Item 59 is a method according to any of items 52 to 57, wherein the first addition stream comprising acrylic acid is incorporated into the reaction chamber of the flow reactor through the first addition port, the second addition stream comprising the halogenating agent is incorporated into the reaction chamber of the flow reactor through the second addition port, and the third addition stream comprising the reaction co-agent and optionally the at least one organic solvent is incorporated into the reaction chamber of the flow reactor through the third addition port.

Item 60 is a process according to any of items 52 to 57, wherein the reaction chamber of the flow reactor further comprises a fourth addition port, and wherein the optional at least one organic solvent is incorporated through the fourth addition port.

Item 61 is a process according to any of items 1 to 51, wherein the reaction product stream is free of solvents, in particular free of organic solvents.

Item 62 is a process according to any of the preceding items, wherein the reactants comprise polymerization inhibitors, in particular polymerization inhibitors selected from the group of phenothiazines and hydroquinones, in particular hydroquinone monomethyl ethers and hydroquinone methyl esters.

Item 63 is a process according to any of the preceding items, which comprises the step of applying a pressure to the reaction product stream in the reaction chamber of the flow reactor, wherein the pressure is a range from 0 to 10 bar, from 1 to bar, from 1 to 8 bar, from 1.5 to 8 bar, from 1.5 to 6 bar, from 2 to 6 bar, from 2 to 5 bar, from 2 to 4 bar, from 2 to 3 bar, or even from 2.5 to 3 bar.

Item 64 is a process according to item 63, wherein the halogenating agent is thionyl chloride.

Item 65 is a process according to any of the preceding items, which is a continuous process.

EXAMPLES

The present disclosure is further illustrated by the following examples. These examples are merely for illustrative purposes only and are not meant to be limiting on the scope of the appended claims.

The following abbreviations are used in this section: NMR=nuclear magnetic resonance, ml=milliliters, min=minutes, mm=millimeters, ppm=parts per million, mol %=mole percent. Abbreviations of materials used in this section, as well as descriptions of the materials, are provided in Table 1.

TABLE 1

| Material | Description |
|---|---|
| AA | acrylic acid, available from Aldrich, Belgium |
| CLA | Chlorinating agent |
| CPC | 3-chloropropionylchloride, obtained in examples |
| $POCl_3$ | phosphoryl trichloride, available from Aldrich, Belgium |
| $SOCl_2$ | thionyl chloride, available from Aldrich, Belgium |
| COl | Oxalyl chloride, available from Aldrich, Belgium |
| DMF | N,N-dimethyl formamide, available from Aldrich, Belgium |

Test Methods and Characterization:

Molar Ratio

The term "Molar ratio" is used throughout this section to mean the ratio or ratios of indicated reactants incorporated into the reaction chamber of the flow reactor.

Conversion Rate

The term "Conversion" is used throughout this section to mean the molar percentage of the carboxylic acid which is actually converted into the corresponding acid chloride. The conversion rate is determined by $^1$H NMR spectroscopy on the unpurified reaction mixture, as described below, under "Characterization."

Characterization

NMR: Analysis by NMR is made using a Bruker Avance 300 Digital NMR spectrometer equipped with Bruker 5 mm BBFO 300 MHz Z-gradient high resolution-ATM probe. The samples are placed in NMR tubes available under the trade designation "WG-5M-ECONOMY" from Aldrich, Belgium. TMS (tetramethylsilane, available from Aldrich, Belgium) is added as a zero ppm reference. Proton NMR spectra are acquired using the following parameters:

Pulse Angle: 30°
Number of Scans: 128
Acquisition Time: 5.3 s
Relaxation time: 2.0 s Except where noted, NMR confirmed the identity of the desired products.

Equipment Employed:

The experiments and reactions are performed using a flow reactor built of PFA-tubing having an inner diameter of 0.50 mm available under the trade designation "IDEX 1512L" from Achrom, Belgium. The flow reactor is a tube reactor having a circular circuitous tube shape, a diameter of about 0.50 mm and a total volume of 3 ml. The flow reactor is suitably connected to syringe pumps commercially available under the trade designation Fusion Touch or Fusion Classic from Chemtrix BV, delivering at least two reactant streams from at least two gas-tight syringes, available under the trade designation "Hamilton Syringe 10 ml 1000 series GASTIGHT" from Hamilton, through PFA tubing with an inner diameter of 1.0 mm, available under the trade designation "IDEX 1507" from Achrom, Belgium, to the reaction chamber of the flow reactor. The gas-tight syringes are connected to the system using an ETFE luer lock (available under the trade designation "IDEX P-628" from Achrom, Belgium) and are mixed together in a ETFE T-connector having a diameter of 0.5 mm (available under the trade designation "IDEX P-632" from Achrom, Belgium). The flow reactor is provided with at least one addition port. The at least two reactant addition streams are incorporated into the reaction chamber of the flow reactor, where a reaction product stream is formed. The reaction product stream exits the flow reactor through a product port and flows through PFA tubing with an inner diameter of 1 mm, connected to the product port using connectors available from Achrom, Belgium, into a collection vessel. In some other examples, the reaction product stream directly exits the flow reactor through the product port. In some examples where a pressure is applied to the reaction product stream in the reaction chamber, the reaction product stream exiting the microflow reactor is connected to a back-pressure regulator (commercially available under the trade designation BPR cartridge "IDEX P-761", from Achrom Belgium), after which the product stream leaves the system. Fittings (available under the trade designation "[IDEX XP-245]" from Achrom, Belgium) are used to make the connections between the tubing and the back-pressure regulator. The flow reactor is heated at the appropriate temperature in an oil bath.

EXAMPLES

Examples 1 to 7 and Comparative Examples 1 to 7

For the examples, the following general procedure is carried out using the flow reactor as described above at the specified temperature. A 10 ml blend solution of acrylic acid and DMF (in the amounts specified in Table 2) is prepared as a first addition stream (Stream I) and incorporated through a first syringe at the flow speed specified in Table 2. The pure halogenating agent (CLA) is incorporated as a second addition stream (Stream II) through a second syringe at the flow speed indicated in Table 2. Comparative examples CE-1 to CE-7 are unsuitable either because of the temperature of the reaction chamber or because of the residence time. The molar ratios of (AA:CLA:DMF) incorporated into the reaction chamber, the nature of chlorinating agent (CLA), the residence time (RT in min), the temperature of the reaction chamber (in ° C.) as well as the conversion rate, determined by $^1$H NMR spectroscopy, are specified in Table 2. Ex.1 and Ex.2 are conducted with a pressure of 2.8 bar.

TABLE 2

Amounts of AA and DMF are indicated in ml
Flow speeds are indicated in ml/min

| Example | Stream I | Stream II | Molar ratios (AA:CLA:DMF) | RT (min) | T (° C.) | Conversion (mol %) |
|---|---|---|---|---|---|---|
| Ex. 1 | AA 6.4 Flow speed 0.07 | DMF 3.6 Flow speed 0.05 | SOCl$_2$ Pure | 1.1:1:0.5 | 25 | 80 | 97 |
| Ex. 2 | AA 9 Flow speed 0.05 | DMF 1 Flow speed 0.05 | SOCl$_2$ Pure | 1.1:1:0.1 | 25 | 80 | 88 |
| CE-1 | AA 9 Flow speed 0.12 | DMF 1 Flow speed 0.13 | SOCl$_2$ Pure | 1.1:1:0.1 | 10 | 20 | 30 |
| Ex. 3 | AA 6.4 Flow speed 0.04 | DMF 3.6 Flow speed 0.03 | POCl$_3$ Pure | 1.1:0:0.5 | 45 | 80 | 84 |
| Ex. 4 | AA 6.4 Flow speed 0.03 | DMF 3.6 Flow speed 0.03 | POCl$_3$ Pure | 1.1:0:0.5 | 25 | 80 | 79 |
| Ex. 5 | AA 6.4 Flow speed 0.04 | DMF 3.6 Flow speed 0.03 | POCl$_3$ Pure | 1:1.0:0.5 | 20 | 80 | 76 |
| Ex. 6 | AA 6.4 Flow speed 0.03 | DMF 3.6 Flow speed 0.03 | POCl$_3$ Pure | 1.1:0:0.5 | 15 | 80 | 75 |
| CE-2 | AA 6.4 Flow speed 0.05 | DMF 3.6 Flow speed 0.05 | POCl$_3$ Pure | 1.1:0:0.5 | 3 | 80 | 12 |

TABLE 2-continued

Amounts of AA and DMF are indicated in ml
Flow speeds are indicated in ml/min

| Example | Stream I | Stream II | Molar ratios (AA:CLA:DMF) | RT (min) | T (° C.) | Conversion (mol %) |
|---|---|---|---|---|---|---|
| CE-3 | AA 6.4 Flow speed 0.16 | DMF 3.6 Pure Flow speed 0.14 | 1.1.0:0.5 | 1 | 80 | 8 |
| CE-4 | AA 6.4 Flow speed 0.03 | DMF 3.6 Pure Flow speed 0.28 | 1.1.0:0.5 | 0.5 | 80 | 6 |
| CE-5 | AA 3.7 Flow speed 0.40 | DMF 6.3 Pure Flow speed 0.20 | 1.1.0:1.5 | 0.5 | 20 | 0 |
| Ex. 7 | AA 6.4 Flow speed 0.05 | DMF 3.6 Pure Flow speed 0.05 | 1.1.1:0.5 | 25 | 80 | 71 |
| CE-6 | AA 6.4 Flow speed 0.27 | DMF 3.6 Pure Flow speed 0.23 | 1.1.1:0.5 | 1 | 80 | 18 |
| CE-7 | AA 9 Flow speed 0.05 | DMF 1 Pure Flow speed 0.05 | 1.1.1:0.1 | 25 | 20 | 23 |

The invention claimed is:

1. A process for the manufacturing of a 3-halopropionylhalide, wherein the process comprises the steps of:
    a) providing a flow reactor comprising a reaction chamber;
    b) providing reactants comprising:
        i. acrylic acid;
        ii. a reaction co-agent selected from the group consisting of N,N- disubstituted amides; and
        iii. a halogenating agent; and
    c) incorporating the reactants into the reaction chamber of the flow reactor, thereby forming a reaction product stream comprising a 3-halopropionylhalide; wherein the molar ratio of acrylic acid to the halogenating agent is 1 to at least 0.8; wherein the temperature of the reaction chamber of the flow reactor is in a range from greater than 60° C. to 120° C.; and wherein the residence time of the reaction product stream comprising the 3-halopropionylhalide in the reaction chamber of the flow reactor is greater than 10 minutes.

2. A process according to claim 1, wherein the temperature of the reaction chamber of the flow reactor is greater than 65° C., after incorporation of the reactants, and in particular the first addition stream, the second addition stream, and the optional third addition stream into the reaction chamber of the flow reactor.

3. A process according to claim 1, wherein the temperature of the reaction chamber of the flow reactor is greater than 70° C., after incorporation of the reactants, and in particular the first addition stream, the second addition stream, and the optional third addition stream into the reaction chamber of the flow reactor.

4. A process according to claim 1, wherein the residence time of the reaction product stream comprising the 3-halopropionylhalide in the reaction chamber of the flow reactor is greater than 12 minutes.

5. A process according to claim 1, wherein the residence time of the reaction product stream comprising the 3-halopropionylhalide in the reaction chamber of the flow reactor is in a range from 15 to 60 minutes.

6. A process according to claim 1, wherein the reaction co-agent is selected from the group consisting of N,N-disubstituted heterocyclic amides and N,N-dialkyl amides, wherein the alkyl group is selected from the group of methyl, ethyl, propyl and butyl.

7. A process according to claim 1, wherein the molar ratio of acrylic acid to the halogenating agent is 1 to at least 0.9.

8. A process according to claim 1, wherein the molar ratio of acrylic acid to the halogenating agent is in a range between 1 to 0.8 and 1 to 2.0.

9. A process according to claim 1, wherein the molar ratio of acrylic acid to the reaction co-agent is 1 to at least 0.1.

10. A process according to claim 1, wherein the molar ratio of acrylic acid to the reaction co-agent is in a range between 1 to 0.1 and 1 to 2.

11. A process according to claim 1, wherein the halogenating agent is selected from the group of chlorinating agents or brominating agents.

12. A process according to claim 1, wherein the halogenating agent is a chlorinating agent selected from the group consisting of thionyl chloride, phosphoryl chloride, oxalyl chloride, phosgene, triphosgene, and any mixtures thereof.

13. A process according to claim 1, wherein the 3-halopropionylhalide is 3chloropropionylchloride or 3-bromopropionylbromide.

14. A process according to claim 1, which further comprises the optional step of incorporating at least one organic solvent into the reaction chamber of the flow reactor.

15. A process according to claim 14, wherein the at least one organic solvent comprises one or more of dichloromethane, methyl ethyl ketone, heptane, cyclohexane, toluene or methyl isobutyl ketone.

16. A process according to claim 1, wherein the temperature of the reaction chamber of the flow reactor is greater than 75° C., after incorporation of the reactants, and in particular the first addition stream, the second addition stream, and the optional third addition stream into the reaction chamber of the flow reactor.

17. The process of claim 1 wherein the process has a conversion rate of acrylic acid into 3-halopropionylhalide of at least 55 mol %, at least 60, mol %, at least 65 mol %, at least 70 mol %, at least 75 mol %, at least 80 mol %, at least 85 mol %, at least 90 mol %, at least 95 mol %, or 97 mol % based on the molar equivalent of acrylic acid.

* * * * *